(12) United States Patent
Shemesh et al.

(10) Patent No.: US 7,887,507 B2
(45) Date of Patent: Feb. 15, 2011

(54) BREAST-FEEDING DEVICE

(75) Inventors: Eldad Shemesh, Binymina (IL); Liat Shemesh-Granot, Binymina (IL); Alexander Babitsky, Moshav Aviel (IL); Orly Babitsky, Moshav Aviel (IL)

(73) Assignee: Tulsa (N.Y.M.) Engineering Solutions Ltd., Tel Aviv (IL)

( * ) Notice: Subject to any disclaimer, the term of this patent is extended or adjusted under 35 U.S.C. 154(b) by 968 days.

(21) Appl. No.: 11/631,378

(22) PCT Filed: Jun. 30, 2005

(86) PCT No.: PCT/IL2005/000702

§ 371 (c)(1),
(2), (4) Date: Dec. 29, 2006

(87) PCT Pub. No.: WO2006/003655

PCT Pub. Date: Jan. 12, 2006

(65) Prior Publication Data

US 2008/0039741 A1    Feb. 14, 2008

Related U.S. Application Data

(60) Provisional application No. 60/584,151, filed on Jul. 1, 2004.

(51) Int. Cl.
*A61M 1/06* (2006.01)
(52) U.S. Cl. ........................................ 604/74

(58) Field of Classification Search ............. 604/73–76, 604/500, 514; 600/584; 73/861; 128/898
See application file for complete search history.

(56) References Cited

U.S. PATENT DOCUMENTS 5,827,191 A    10/1998   Rosenfeld
6,109,100 A *  8/2000   Buckley et al. ............... 73/198

FOREIGN PATENT DOCUMENTS

WO         01/54488        8/2001
WO       2005/016220       2/2005

* cited by examiner

*Primary Examiner*—Nicholas D Lucchesi
*Assistant Examiner*—Nathan R. Price
(74) *Attorney, Agent, or Firm*—The Nath Law Group; Susanne M. Hopkins; Robert T. Burns

(57) ABSTRACT

The present invention provides a device and method for measuring the amount of milk supplied to a feeding infant. The device (10) comprises a cap (13) having a nipple-shaped region (10) with an inner surface (14) and an outer surface (16) and a duct (18) extending therebetween. The duct has an inlet (20) at the inner surface and an outlet (22) at the outer surface. The cap is adapted to be mounted on the nipple region of a woman's breast with the inner surface facing the woman's breast and to allow breast-milk to pass through the duct. The device further comprises a sensor (24) associated with the duct for measuring at least milk volume passing through the duct and providing data indicative of the volume. The sensor is embedded between the inner and outer surface of the cap

32 Claims, 3 Drawing Sheets

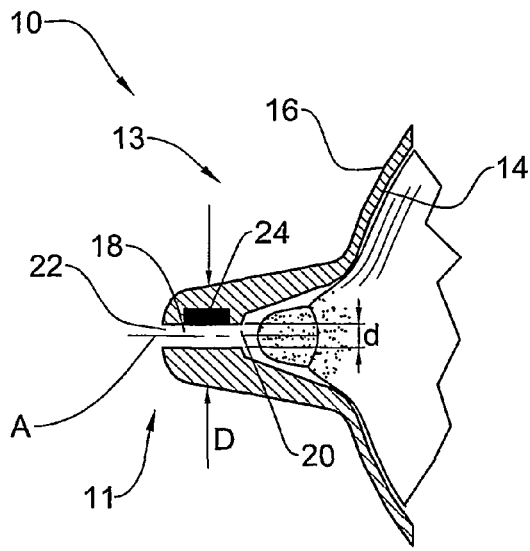
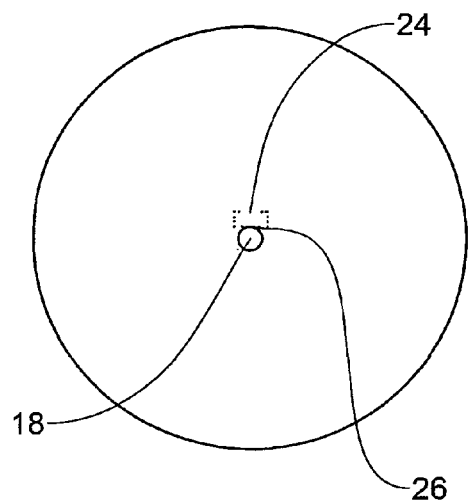
FIG. 1  FIG. 2
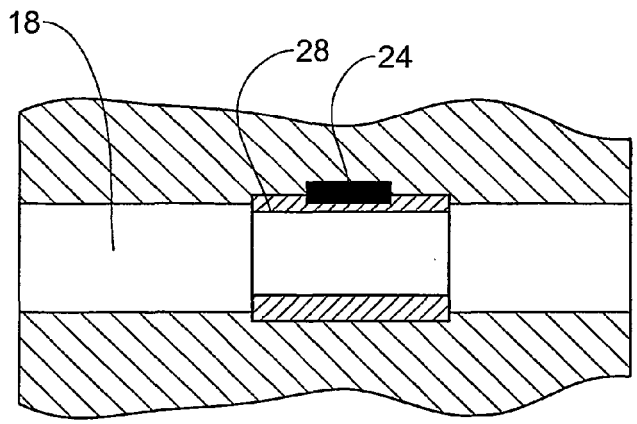
FIG. 3A
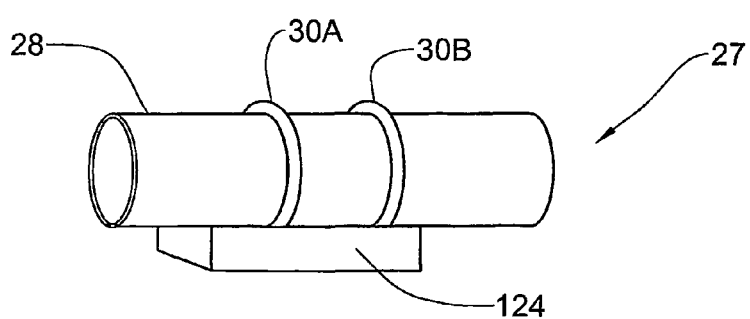
FIG. 3B

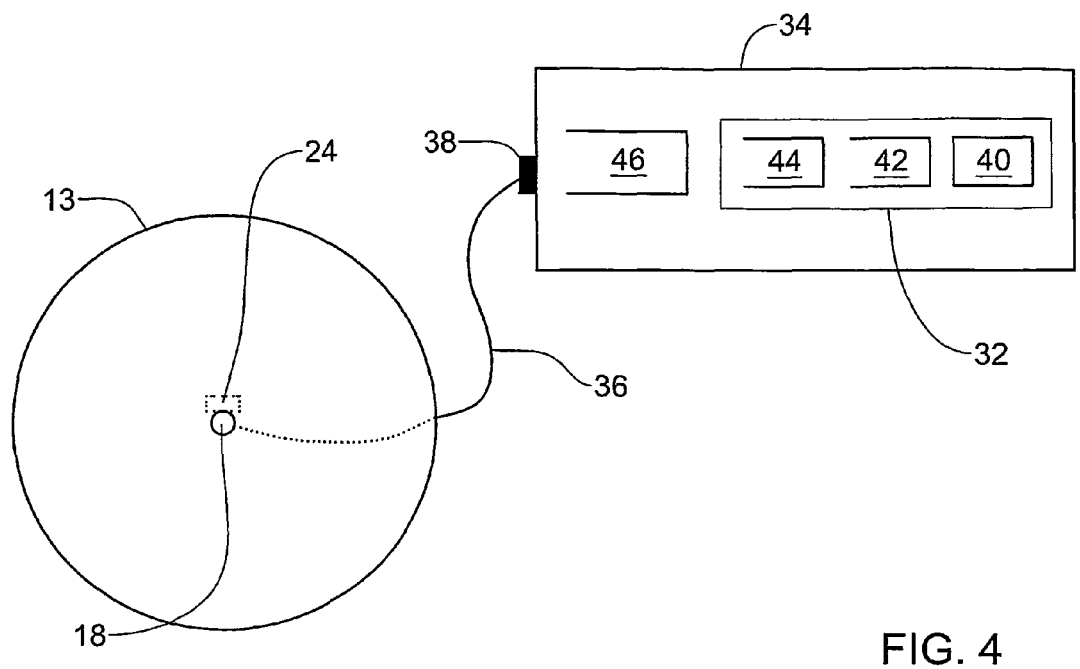
FIG. 4
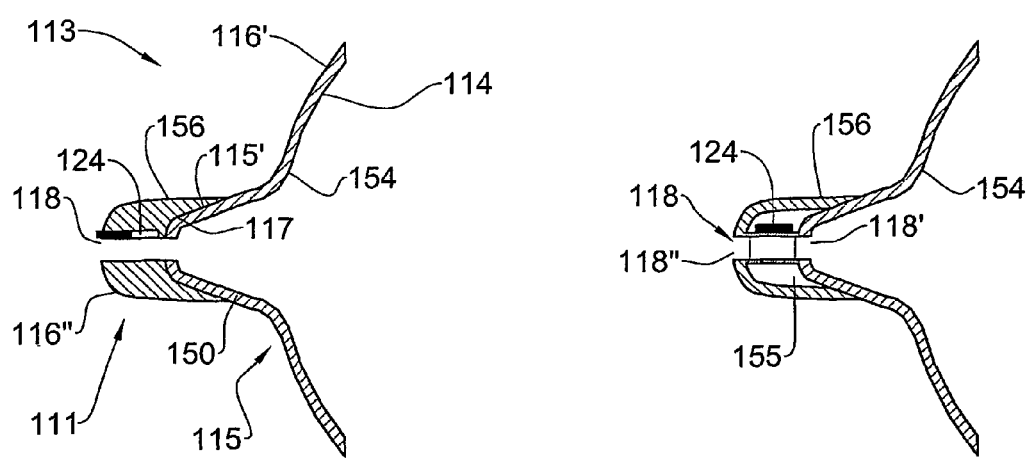
FIG. 5A                    FIG. 5B

US 7,887,507 B2

BREAST-FEEDING DEVICE

Cross-Reference:

This is a National Phase Application filed under 35 U.S.C. 371 of International Application No. PCT/IL2005/000702, filed Jun. 30, 2005, claiming the benefit under 35 USC 119(e) of U.S. Provisional Application No. 60/584,151, filed Jul. 1, 2004, the entire contents of each of which is hereby incorporated herein by reference in its entirety.

FIELD OF THE INVENTION

This invention relates to infant care products and in particular to a device and method for determining milk volume extracted from a breast during a breast-feeding session.

BACKGROUND OF THE INVENTION

More than two decades of research have established that breast milk is one of the most valuable contributors to infant health. Breast-fed infants have lower rates of hospital admissions, ear infections, diarrhea, rashes, allergies, and other medical problems than bottle-fed babies. Further, increased breast-feeding rates save consumers money, spent both on infant formula and in health-care.

The benefits of breast feeding are well recognized. The primary benefit is nutritional. Human milk contains just the right amount of fatty acids, lactose, water, and amino acids for human digestion, brain development, and growth. Further, breast-fed infants have fewer illnesses because human milk transfers to the infant a mother's antibodies to disease. About 80 percent of the cells in breast milk are macrophages, cells that kill bacteria, fungi and viruses. Breast-fed infants are thus protected, in varying degrees, from a number of illnesses, including pneumonia, botulism, bronchitis, staphylococcal infections, influenza, ear infections, and German measles. Furthermore, mothers produce antibodies to whatever disease is present in their environment, making their milk custom-designed to fight the diseases their infants are exposed to as well.

Lack of knowledge as to how much an infant consumed during a feeding session has led to the developments of devices and techniques for determining breast-milk consumption. One well known method of determining milk volume during breast feeding involves measurement of an infant's weight before and after feeding. However, this method is inconvenient as the infant needs to be naked and still during measurement, does not provide real-time value for how much the infant consumed and typically requires very expensive accurate digital weight scales.

A device for measuring milk volume during breast feeding is described in each of U.S. Pat. No. 5,827,191 and in WO01/54488. The device comprises a flexible cap-shaped cover including an outer surface, an inner surface and a passage extending between the inner and outer surface. The cap is adapted for mounting on a woman's breast such that the inner surface faces the breast and the passage faces the nipple. The device also includes a micro measurement volume sensor, located in front of the passage between the inner surface of the cap and the woman's nipple for measuring the milk volume entering the passage.

SUMMARY OF THE INVENTION

According to one aspect of the present invention, there is provided a device for measuring the amount of milk supplied to a feeding infant. The device comprises a cap having a nipple-shaped region with an inner surface, an outer surface and a duct extending therebetween. The duct has an inlet at the inner surface and an outlet at the outer surface. The cap is adapted to be mounted on the nipple region of a woman's breast with the inner surface facing the woman's breast, and to allow breast-milk, when sucked by the infant, to pass through the duct. The device further comprises a sensor associated with the duct for measuring at least milk volume passing through the duct and providing data indicative of the volume. The sensor is embedded between the inner and outer surfaces of the nipple-shaped region of the cap.

Hereinafter in the specification and claims, the term "sensor" is to be understood as referring to any sensing device, or combination thereof. Further, the terms "measuring" or "measurement" are to be understood as referring to direct as well as indirect measurement. Indirect measurement denotes the determination of a parameter from which at least the milk volume may be calculated, e.g. flow velocity. Yet, further, the term "association," when used in the specification and claims with reference to the sensor and the duct, is to be understood as indication that the sensor is so connected with the duct as to allow for the measurement defined above.

The cap may be formed from one piece or may be multi-layered. For example, it may be constructed from an internal and an external layer, at least at said nipple-shaped region, the internal layer comprising said inner surface, and the external layer comprising said outer surface. The internal layer may have a substantially uniform thickness along the nipple-shaped region and along the internal layer periphery surrounding the nipple-shaped region. The external layer may be in the form of the nipple-shaped region with essentially no periphery surrounding it. Alternatively, the internal layer may have a nipple-shaped region and a periphery and maybe thicker at the former than the latter. In both cases, the thickness of the external layer at the nipple-shaped region may be greater than that of the internal layer.

The sensor may be a mechanical sensor, a temperature gradient sensor, or any other suitable sensor. The device may further comprise at least one additional sensor adapted to measure one or more of the following parameters of the milk flowing through said duct: temperature, viscosity; fat content, chemical presence.

The device may further comprise a control unit in communication with said sensor(s), for receiving from the sensor(s) said data and providing an output. The output comprises at least one real-time value indicative of the volume of milk passing through said duct.

According to another aspect of the present invention, there is provided a method for real-time measurement of the amount of milk supplied to a feeding infant. The method comprises the steps of providing a device, as described above, for performing the measurement, mounting the device on a woman's breast with the inner surface of the nipple-shaped region facing the women's nipple, and allowing an infant to breastfeed from the breast through the duct.

BRIEF DESCRIPTION OF THE DRAWINGS

In order to understand the invention and to see how it may be carried out in practice, exemplary embodiment will now be described, by way of non-limiting examples only, with reference to the accompanying drawings, in which:

FIG. 1 is a schematic longitudinal cross-sectional view of a real-time measuring device according to one embodiment of the invention;

FIG. 2 is a schematic front view of the real-time measuring device of FIG. 1;

FIG. 3A is an enlarged schematic longitudinal cross-sectional view of the duct in the cap shown in FIG. 1, in accordance with an alternative embodiment of the invention;

FIG. 3B is a schematic perspective view of a measuring unit mounted in the duct of FIG. 3A;

FIG. 4 illustrates schematically the real-time measuring device shown in FIG. 2, with a control unit;

FIG. 5A-5B are schematic longitudinal cross-sectional views of a measuring device according to alternative embodiments of the invention;

DETAILED DESCRIPTION OF EXEMPLARY EMBODIMENTS

Figure 5C:
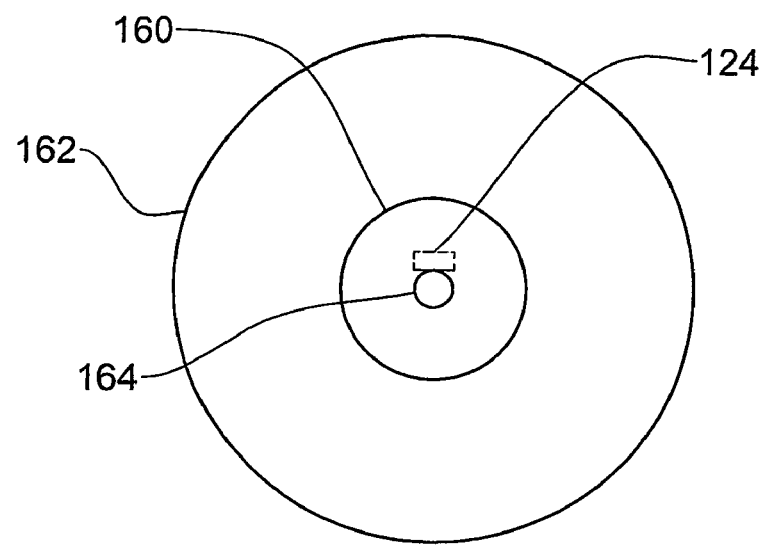
FIG. 5C is a schematic front view of the device illustrated in FIGS. 5A and 5B.

A real-time measuring device 10 according to one embodiment of the present invention is schematically shown in FIG. 1, when mounted onto a woman's breast. According to this embodiment, the device comprises a cap 13 having a nipple-shaped region 11, with an inner surface 14 configured to generally match the contour of a woman's breast, an outer surface 16 and a duct 18 extending between the inner surface 14 and outer surface 16 along a longitudinal axis A. The duct 18 has an inlet 20 located at a proximal end thereof at the inner surface 14, and an outlet 22 located at a distal end thereof (at the outer surface 16). As seen in FIG. 1 and also FIG. 2, the device is further equipped with a sensor 24 for measuring the volume of milk passing through the duct 18 along the axis A from the inlet 20 to the outlet 22. The sensor 24 and provides data indicative of the milk volume.

As further shown in FIG. 1, the sensor 24 is embedded between the inner surface 14 and the outer surface 16 of the nipple-shaped region 11 of the cap 13 at a location, where the cross-sectional area of the duct 18 constitutes a minority of the cross-sectional area of the nipple-shaped region. In FIG. 1, these cross-sectional areas are defined, respectively, by a diameter d of the duct 18 and a diameter D of the nipple-shaped region 11. The ratio between the cross-sectional areas (or between the diameters d and D) may for example be in the range of 0.05 to 0.5. Clearly, the duct having such dimension is designed to prevent a woman's nipple to enter it, due to which the sensor is prevented from contact with a woman's nipple during a measurement session. The measurement session may last for the entire duration of a breast-feeding session (i.e., from latching until the cessation of suckling) or for a predetermined portion thereof (e.g., for the first ten minutes of feeding, etc.).

The sensor 24 may be mounted in or adjacent to the duct in such association therewith as to allow for the required measurement. When the sensor is mounted outside the duct adjacent thereto, it may be either exposed at least partially to the interior of the duct or adapted to perform measurements outside the duct. The measurements may be indicative of at least the milk volume. Thus, for example, the duct 18 may comprise an essentially rigid section, e.g., a tube embedded in at least part of the duct 18, to which the sensor may be attached by any means known per se, such as clasping, hanging, adhering, etc., as described in more detail below.

FIG. 3A is a schematic cross-sectional view of a portion of the nipple-shaped region 11 of the cap illustrated in FIG. 1. A measuring unit 27 comprising a tube 28 and the sensor 24 is embedded in the duct 18. The tube 28 may extend only along a portion of the duct 18, as illustrated in FIG. 3A, or along the entire duct, i.e., spanning the entire length of the duct from inlet 14 to outlet 16 (not shown). FIG. 3B is a schematic perspective view of the measuring unit 27, illustrating how the sensor 24 may be mounted to the tube 28 by means of two hook-like structures 30A, 30B. Alternatively, the sensor 24 may be associated with tube 28 by other means, such as by means of adhesive material. The sensor 24 may also be associated with the duct 18 directly, i.e., without the use of a tube. For this purpose, the cap may be formed for example, by producing, with a space or a suitable groove in the interior thereof, into which the sensor may be embedded. Alternatively, the sensor may be attached to the interior of the duct by any suitable means.

The sensor may be a single sensor or a combination of sensors. The sensor 24 is preferably a flowmeter adapted to determine the velocity and/or volume of milk flowing through duct 18. The measurement of the volume may be an indirect determination, i.e. by measuring the temperature gradient along the tube 28 as mentioned hereinbefore, and calculating from the measured temperature gradient the corresponding milk volume passing through the duct 18. In addition, the sensor 24 may also measure other parameters, such as the temperature, viscosity, fat content, etc., of the expressed milk. It may also detect the presence of chemicals or biological matter, such as pro-inflammatory or inflammatory agents, which may suggest the development or existence of an infection (e.g. mastitis) or any other pathological state.

The measuring device may typically comprise additional components, such as a control unit 32 in communication with the sensor 24. As shown in FIG. 4, the control unit 32 is configured to receive a data stream from the sensor and to provide an output comprising real-time values of parameters sensed by the sensor. The control unit 32 is embedded in a housing 34 being connected to the sensor 24 by a communication cable 36. The communication cable 36 comprises a connector 38 specially adapted to connect to the sensor 24. As further shown in FIG. 4, the connector 38 may be located on the control unit to which a communication cable 36, extending from the cap 13, is to be connected. Alternatively, the connector 38 may be located on the cap 13, preferably at the perimeter of the cap (not shown). The control unit 32 further comprises a processing unit 40 adapted to obtain the data stream from the sensor 24, and to carry out data analysis consisting of processing the data stream into values corresponding to the volume of milk passing through the duct 18 during a measurement session. The processing unit 40 is also adapted to provide these values as output. The output may be a single value indicating the volume of milk supplied during the measurement session, or a series of values delineated by time intervals during the session. For example, the processing unit 40 may provide as output a sequence of values, e.g. a value every minute, the sum of which provides the total volume supplied during a complete feeding session. This may allow the mother at each time point (in this particular example, every minute) to determine if the infant is actually being fed or is merely pacifying himself by suckling without actually consuming milk. An example of a processing unit which may be utilized in the present invention is that provided by Intel, 8051 microcontroller (Intel, USA).

Alternatively, the control unit 32 within housing 34 may be is embedded in the outer surface of the cap 13, preferably at the perimeter thereof (not shown).

The control unit 32 may also be equipped with a storage medium 42 for receiving and storing the data stream transmitted either directly from the sensor 24 and/or the processed data transmitted from the processing unit 40. The storage medium 42 may be integral to the control unit, such as by providing a hard disk or other volatile or non-volatile media (flash memory), or may be external thereto. Alternatively, an output interface (not shown) may be provided to send data to a standard computer.

The control unit 32 may further be equipped with a user interface 44 designed to assist in the operation and performance of the measuring device. For example, the user interface 44 may be adapted to enable or disable the operation of the device, e.g., by the use of an on/off button, and may enable initiation or termination of a measurement session, e.g., by the use of start/stop/pause/reset buttons.

The user interface 44 may also be designed to enable input from the user of parameters necessary for a specific measurement, such as a desired time window for measurement. For example, a mother who wishes to measure the volume of the milk expressed during the first 10 minutes of a breast feeding session lasting an arbitrary length of time may define a time window of 10 minutes for the measurement session.

The user interface 44 may further be provided with means to enable the user to retrieve data, such as values of an earlier measurement, from the storage utility 42. This allows the mother (or other user) to compare different measurement sessions and monitor the eating behavior of the infant over the course of a day, a week, etc.

The measuring device 10 may also comprise a display utility 46 connectable to the processing unit 40 and adapted to receive from the processing unit 40 one or more values, including a value indicative of the volume of milk supplied to the infant during a measurement session, and to display thereupon the measure values. In addition, the display unit 46 may display additional parameters, including, but not limited to, the date and time a value was obtained, the length of a particular measurement session, etc. The display utility may be positioned on a nearby table, or may be attached to the mother's clothing (e.g. the shirt or bra) by a security pin or clipper. In any case, display utility may be equipped with means for adjusting the angle of display.

The display unit 46 may provide a graph of the different values retrieved during a measurement session or a graph of the values retrieved during a sequence of feeding sessions. Further, since the processing unit 40 provides values corresponding to real-time measurements, the display utility 46 may also be designed to provide the mother with real-time warnings, such as if undesired matter is supplied to the infant (e.g., when the mother is suffering from a yet undetected mastitis), or in case the infant fell asleep (or is about to fall asleep). These warnings may be provided by visual and/or audio means.

The control unit 32 may be located proximal to the sensor 24 or at a remote site (e.g., a hospital may wish to measure the breastfeeding rate of a patient and collect or view this data in a central location, such as a nurse's station). The control unit 32 may receive data from the sensor 24 wirelessly by use of a specially adapted transmitter, or may receive the data by means of a communication cable, as illustrated in FIG. 4. Similarly, the display utility 46 may also be proximal to the control unit 32, i.e. enclosed in housing 34, or at a remote site and connected to the control unit 32 by communication cable or wirelessly (not illustrated).

The measuring device 10 is equipped with one or more power sources (not shown) to provide the different components of the device with power. The power source may be a battery pack or a power supply adapted to convert an AC input into an appropriate DC voltage.

The control unit 32, the display utility 46, and the power source may be located in the detachable housing 34. The housing may be located at a remote area from the cap 13 and connected thereto as described above. Alternatively, the housing 34 may be adapted to be mounted on the cap 13. To this end, the cap may be constructed to enable simple attaching, such as by clipping, of the housing 34 to the cap and, when necessary, e.g., in order to sterilize the cap 13 or replace a power source, the housing may be easily detached. This permits safe sterilization of the cap without the risk of damaging the control unit.

While not specifically illustrated herein, the cap may comprise more than one duct through which extracted milk may flow. Each duct is equipped with its own sensor. A control unit, adapted to simultaneously receive several data streams in parallel, is connected to each sensor.

The cap is typically made of a durable, non-toxic, flexible, preferably elastic material, as known to those versed in the nursing and infant care industry, such as silicone (natural rubber, latex) and isoprene.

Reference is now made to FIG. 5A and FIG. 5B which illustrate examples of two constructions of a cap of a measuring device according to alternative embodiments of the invention.

FIG. 5A illustrates a cap 113 constructed from two layers of flexible material (which may be of the same or different kind), namely an internal layer 154 and an external layer 156. The internal layer 154 has an inner surface 114, an outer surface 115, a nipple area 150 and a duct 118 in the nipple area, extending between the inner and outer surface. The outer surface 115 of the inner layer has a nipple portion 115' and a peripheral portion 116'. The external layer 156 is attached to nipple portion of the outer surface of 115 of the internal layer 154. The external layer 156 is in the form of a tip reliably attached to the internal layer at the nipple portion 115' of its outer surface 115. The tip 156 has an outer surface 116" and an inner surface 117 suiting in shape to the nipple portion 115' of the outer surface of the internal layer 154. Both the internal and the external layers are formed with ducts, (not designated) and the external layer is so attached to the internal layer that their ducts are aligned to form a duct 118. Outer surface 116" of the external layer or tip 156 and the peripheral portion 116' of the outer surface 115 of the internal layer 154 constitute outer surface of the nipple-shaped region 111 of the cap 113. Embedded in the tip 156 is the sensor 124, which is associated with the duct 118 The tip 156 may have a periphery extending over a part of or over the entire periphery or internal layer 154.

As seen, the internal layer 154 has an essentially uniform relatively small thickness, whilst the tip 156 is relatively thicker to enable the sensor to be embedded therein.

FIG. 5B illustrates a measuring device similar to that illustrated in FIG. 5A, however, with the external layer 156 being relatively thin. Both the internal and external layers are formed with respective duct portions 118' and 118" and the external layer is attached to the internal layer along a circular area spaced from the duct 118'. The external layer 156 is spaced from the internal layer 154 by a space 155, in which a tube 128, constituting a duct, is mounted for connecting the ducts 118' and 118" of two layers and for providing a passage 118 for flowing therethrough of expressed milk. The sensor 124 is located within the space 155, in association with the tube 128.

In both the above embodiments shown in FIGS. 5A and 5B, the two layers may be heat-welded, heat-pressed (compressing), glued to each other or by any other means known to those versed in the art.

Furthermore, the internal layer may be in the form of a commercially available nipple protector (for example, such as nipple protectors available from Avent, USA), whilst the external layer may be in the form of a preformed tip with the sensor embedded therein or attached thereto.

FIG. 5C is a schematic front view of the cap 113 and sensor 124 shown in FIGS. 5A and 5B, illustrating the periphery of the internal layer designated as 160, the periphery of the external layer designated 162 and the duct designated 164, in association with sensor 124.

It will be appreciated that according to all the above embodiments of the measuring device, the sensor is to be embedded between the inner surface of the nipple-shaped region of the cap and the outer surface thereof, such that when the measuring device is placed onto a woman's breast, contact exists between the sensor and the breast. This allows the measuring device to avoid any abrasion to the breast or other inconveniences which may be caused by a sensor located at the inner surface of the cap, as in hitherto known breast feeding devices.

As mentioned above, the sensor may be any micro flow measurement (flowmeter) device, as known to those versed in the art. For example, the flowmeter may be a thermal flow measurement device comprising a tube and a temperature sensor measuring the outer tube temperature gradient. The temperature gradient is proportional to the mass of milk passing through the tube, from which the volume is then calculated. Thermal flowmeters are commercially available, e.g. from Sensirion AG, Switzerland.

Figure 6:
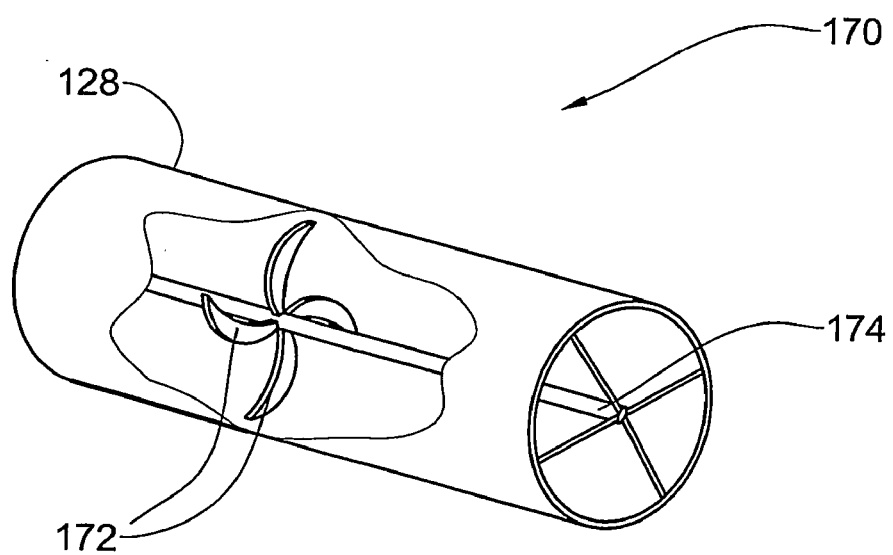
FIG. 6 is a partial cutaway view of a flowmeter for use with the measuring device illustrated in FIG. 1, in accordance with a still further alternative embodiment of the invention.

Alternatively, the measuring unit may comprise a mechanical flow volume sensor. FIG. 6 illustrates a measuring unit comprising a propeller type mechanical flowmeter 170 with a shaft 172 carrying radially extending curved blades 174, typically between two to six in number. The shaft 172 and blades 174 are encapsulated within a housing 128, e.g. a tube, while allowing the blades to freely rotate thereabout. The flowmeter is disposed within the duct such as duct 18 in FIG. 1, or 118 in FIGS. 5A and 5B, so that all expressed milk will pass therethrough. In operation, milk extracted from the breast passes through the housing 128 and thrusts the blades 174 at a speed (revolutions per unit time) which is proportional to the volume of milk passing through the housing 128. Propeller type flowmeters are available, such as those manufactured by Microtec (Micro Tec Gesellschaft fuer Mikrotechnologie mbH, German).

Those skilled in the art to which this invention pertains will readily appreciate that numerous changes, variations and modifications can be made without departing from the scope of the invention mutatis mutandis.

The invention claimed is:

1. A device for measuring the amount of milk supplied to a nursing infant, the device comprising:
   (a) a cap having a nipple-shaped region with an innermost surface and an outermost surface and a duct extending therebetween and having a longitudinal axis, the duct having an inlet at the inner surface and an outlet at the outer surface, the cap adapted to be mounted on the nipple region of a woman's breast with the innermost surface facing the woman's breast; and to allow breast-milk to pass through said duct along its longitudinal axis;
   (b) a sensor associated with said duct for measuring at least milk volume passing through said duct and providing data indicative of said volume, wherein said sensor is embedded at a location between said innermost surface and outermost surface of said nipple-shaped region of the cap, said sensor being spaced from the inlet of the duct towards the outlet of the duct along the duct's longitudinal axis and having an extension along the longitudinal axis of the duct, that is greater than its extension transverse to said axis; and
   (c) a cross-sectional area which each of the nipple-shaped region and the duct has at said location, the cross-sectional area of the duct occupying a minority of the cross-sectional area of the nipple-shaped region.

2. The device of claim 1, further comprising a control unit in communication with said sensor, for receiving from the sensor said data and providing an output comprising at least one real-time value indicative of the volume of milk passing through said duct.

3. The device of claim 2, wherein said control unit comprises a display unit and/or a user interface.

4. The device of claim 3, wherein said control unit is encapsulated in a detachable housing, the housing being associated with the outer surface of the cap.

5. The device of claim 3, wherein said control unit is encapsulated in housing, the housing being located at a remote site from the cap.

6. The device of claim 1, wherein said cap is constructed from an internal layer comprising the inner surface and an external layer comprising at least a part of the outer surface of at least the nipple-shaped region of said cap.

7. The device of claim 6, wherein the external layer is in the form of a tip attached to the internal layer.

8. The device of claim 7, wherein said sensor is embedded in or attached to said tip.

9. The device of claim 7, wherein said tip is thicker than said internal layer at least at said nipple-shaped region.

10. The device of claim 1, wherein the duct holds a tube.

11. The device of claim 10, wherein said tube is located within the duct so that it is spaced at least from the inlet of the duct.

12. The device of claim 10, wherein said sensor is associated with said tube.

13. The device of claim 1, further comprising a tip having a duct and a sensor associated with said duct for measuring parameters of milk passing through the duct, wherein the tip is configured to be reliably attached to a nipple protector.

14. A device for measuring the amount of milk supplied to a nursing infant, the device comprising:
   (a) a cap having a nipple-shaped region with an inner surface and an outer surface and a duct extending therebetween, the duct having an inlet at the inner surface and an outlet at the outer surface, the cap adapted to be mounted on the nipple region of a woman's breast with the inner surface directly facing the woman's breast; and to allow breast-milk to pass through said duct; and
   (b) a sensor associated with said duct for measuring at least milk volume passing through said duct and providing data indicative of said volume, wherein said sensor is embedded at a location between said inner surface and outer surface of said nipple-shaped region of the cap, which is spaced from the inlet of the duct in a direction towards the outlet of the duct, and at which the nipple-shaped region has a cross-sectional area whose minority is occupied by the duct's cross-sectional area, the nipple-shaped region having a longitudinal axis and, in its longitudinal cross-sectional view, the sensor and the duct having corresponding dimensions in a direction perpendicular to said longitudinal axis, the dimension of the sensor not exceeding the dimension of the duct.

15. The device of claim 14, wherein said sensor is a mechanical sensor or a temperature gradient sensor.

16. The device of claim 14, comprising at least one additional sensor operable to measure at least one parameter of the milk flowing through said duct, the parameter being selected from a list consisting of temperature, viscosity, fat content, and chemicals presence.

17. A method for real-time measurement of the amount of milk supplied to a nursing infant, the method comprising:
  providing a device according to claim 14, for executing said measurement;
  mounting said device on a woman's breast with the inner surface of the nipple-shaped region facing the woman's nipple; and
  allowing an infant to breast feed from said breast through said duct.

18. The method of claim 17, for measuring the amount of milk supplied to the infant during a predetermined time window within a breast feeding session.

19. The device of claim 14, having two layers, a first layer providing said inner surface and a second layer providing said outer layer surface, wherein said first layer is adapted for being in direct contact with the woman's breast.

20. The device of claim 19, wherein the device is free of any layer separating, during its use, said first layer from the woman's breast.

21. The device of claim 14, wherein the sensor has an extension along a longitudinal axis of the duct, that is greater than an extension transverse to said axis.

22. The device of claim 14, wherein the nipple-shaped region has a longitudinal axis and, in a longitudinal cross-sectional view, the sensor and the duct have corresponding dimensions in a direction perpendicular to said longitudinal axis, a dimension of the sensor not exceeding a dimension of the duct.

23. The device of claim 14, wherein the sensor occupied a minority of said cross-sectional area of the nipple-shaped region.

24. The device of claim 14, further comprising a control unit in communication with said sensor, for receiving from the sensor said data and providing an output comprising at least one real-time value indicative of the volume of milk passing through said duct.

25. The device of claim 14, wherein said cap is constructed from an internal layer comprising the inner surface and an external layer comprising at least a part of the outer surface of at least the nipple-shaped region of said cap.

26. The device of claim 25, wherein the external layer is in the form of a tip attached to the internal layer.

27. The device of claim 26, wherein said sensor is embedded in or attached to said tip.

28. The device of claim 26, wherein said tip is thicker than said internal layer at least at said nipple-shaped region.

29. The device of claim 14, wherein the duct holds a tube.

30. The device of claim 29, wherein said tube is located within the duct so that it is spaced at least from the inlet of the duct.

31. The device of claim 29, wherein said sensor is associated with said tube.

32. The device of claim 14, further comprising a tip having a duct and a sensor associated with said duct for measuring parameters of milk passing through the duct, wherein the tip is configured to be reliably attached to a nipple protector.

* * * * *